(12) United States Patent
Ohno et al.

(10) Patent No.: US 8,415,273 B2
(45) Date of Patent: Apr. 9, 2013

(54) BROADLEAF PERENNIAL WEED CONTROL AGENT FOR GRASS, AND METHOD FOR CONTROLLING BROADLEAF PERENNIAL WEEDS IN GRASS

(75) Inventors: Akira Ohno, Chiba (JP); Yasuji Okunishi, Inba-gun (JP); Takashi Sato, Chiba (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 12/525,363

(22) PCT Filed: Feb. 1, 2008

(86) PCT No.: PCT/JP2008/051656
§ 371 (c)(1),
(2), (4) Date: Jul. 31, 2009

(87) PCT Pub. No.: WO2008/096675
PCT Pub. Date: Aug. 14, 2008

(65) Prior Publication Data
US 2010/0113277 A1 May 6, 2010

(30) Foreign Application Priority Data

Feb. 6, 2007 (JP) .................................. 2007-027072

(51) Int. Cl.
*A01N 43/653* (2006.01)
(52) U.S. Cl. ...................................................... 504/273
(58) Field of Classification Search .................. None
See application file for complete search history.

(56) References Cited

U.S. PATENT DOCUMENTS

| | | | |
|---|---|---|---|
| 4,795,484 A | 1/1989 | Aoki et al. | |
| 4,820,334 A | 4/1989 | Shida et al. | |
| 4,973,353 A * | 11/1990 | Shida et al. | 504/273 |
| 5,077,413 A | 12/1991 | Bohner et al. | |
| 6,734,139 B1 * | 5/2004 | Feucht et al. | 504/128 |

FOREIGN PATENT DOCUMENTS

| JP | 04-005282 | 1/1992 |
|---|---|---|
| JP | 2003-261405 | 9/2003 |

OTHER PUBLICATIONS

Test results for grass-related herbicides and growth regulators, published Dec. 2003 by The Japan Association for Advancement of Phyto-Regulators, pp. 168-195.*

Japanese Patent Office, International Search Report (translated) mailed Mar. 25, 2008, from related International Patent Application No. PCT/JP2008/051656.
Narumi Shibuya et al., Shibuya Index—2007 (12th Edition), Kabushiki Kaisha Zenkoku Noson Kyoiku Kyokai, Jun. 25, 2007, p. 211.
Spring-Summer 2003 edition, Test results for grass-related herbicides and growth regulators, published Dec. 2003 by The Japan Association for Advancement of Phyto-Regulators, pp. 168-195. (English-language abstract provided).
Japanese Office Action for JP Application No. 2008-557083, dated Feb. 28, 2012, 6 pages.

* cited by examiner

*Primary Examiner* — Alton Pryor
(74) *Attorney, Agent, or Firm* — Kenyon & Kenyon, LLP

(57) ABSTRACT

The present invention provides a broadleaf perennial weed control agent for grass, which has a powerful herbicide effect on weeds that have proven difficult to control with conventional herbicides for grass and/or on weeds having resistance to conventional herbicides, and yet is safe for use on grasses; and a method for controlling broadleaf perennial weeds in grass by applying the control agent to the soil or the foliage. The present invention provides a broadleaf perennial weed control agent for grass, including a 1,5-diphenyl-1H-1,2,4-triazole-3-carboxamide derivative represented by a formula (1) as an active ingredient, and a method for controlling broadleaf perennial weeds in grass that includes applying the control agent to the soil or foliage:

[Chemical Formula 1]

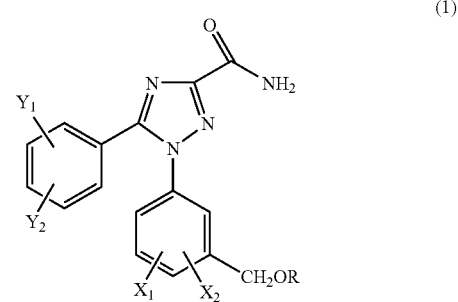

(1)

wherein R represents an alkyl group of 1 to 10 carbon atoms that may be substituted with a fluorine atom and the like, $X_1$ represents a halogen atom or an alkyl group of 1 to 3 carbon atoms, $X_2$ represents a hydrogen atom or a halogen atom, and $Y_1$ and $Y_2$ each independently represents a hydrogen atom or a fluorine atom.

3 Claims, No Drawings

BROADLEAF PERENNIAL WEED CONTROL AGENT FOR GRASS, AND METHOD FOR CONTROLLING BROADLEAF PERENNIAL WEEDS IN GRASS

TECHNICAL FIELD

The present invention relates to a broadleaf perennial weed control agent for grass containing a 1,5-diphenyl-1H-1,2,4-triazole-3-carboxamide derivative as an active ingredient, and also relates to a method for controlling broadleaf perennial weeds in grass that includes applying the control agent to the soil or to the foliage of the weed.

Priority is claimed on Japanese Patent Application No. 2007-027072, filed Feb. 6, 2007, the content of which is incorporated herein by reference.

BACKGROUND ART

Turf grass is used for a variety of purposes, such as maintaining appearances, preventing fires and providing recreation space within golf courses, parks, household gardens, river bed, and orchard grounds and the like.

One of the problems associated with maintaining appearances while ensuring healthy growth of the grass is the control of weeds. Further, weeds that multiply within grass can inhibit growth of the grass, and the seeds of those weeds can stick to clothing and provide breeding grounds for insect pests.

Accordingly, weeds that multiply within grass have conventionally been controlled using a herbicide. However, in control methods using conventional herbicides, a variety of problems tend to arise, including a narrow weed killing spectrum for the herbicide, leading to an unsatisfactory control effect, restrictions in terms of the treatment method, a narrow timeframe for optimum treatment, and environmental safety issues.

Furthermore, in recent years, weeds that have developed resistance due to repeated application of the same herbicides have also become problematic.

In relation to the present invention, the fact that 1,5-diphenyl-1H-1,2,4-triazole-3-carboxamide derivatives exhibit a herbicide activity has already been disclosed in Patent Document 1 and the like. Flupoxam, which is one of the compounds disclosed in this document (ISO name: flupoxam; CAS name: 1-[4-chloro-3-[(2,2,3,3,3-pentafluoropropoxy)methyl]phenyl]-5-phenyl-1H-1,2,4-triazole-3-carboxamide, Reg. No. 119126-15-7), has been registered in Europe as a herbicide for wheat and barley.

Furthermore, flupoxam has also been supplied to The Japan Association for Advancement of Phyto-Regulators for testing as a soil-based herbicide for grass in 2002. It is known that flupoxam has no detrimental effects on turf grasses such as *Zoysia japonica* and *Zoysia tenuifolia*, while exhibiting a powerful control action on broadleaf annual weeds such as chickweed and gramineous weeds such as crabgrass that can grow in grass (see Non-Patent Document 1).

However, until now it was not known that flupoxam also exhibits excellent weed control activity for broadleaf perennial weeds that grow in grass, and weeds that have resistance to conventional herbicides.

[Patent Document 1]
Japanese Unexamined Patent Application, First Publication No. S63-313779

[Non-Patent Document 1] Spring-summer 2003 edition of test results for grass-related herbicides and growth regulators—(published December 2003 by The Japan Association for Advancement of Phyto-Regulators)

DISCLOSURE OF INVENTION

Problems to be Solved by the Invention

The present invention takes the above issues associated with the conventional technology into consideration, and has an object of providing a broadleaf perennial weed control agent for grass, which exhibits a powerful herbicide effect on weeds that have proven difficult to control with conventional herbicides for grass and/or on weeds having resistance to conventional herbicides, and yet is safe for use on grasses, as well as providing a method for controlling broadleaf perennial weeds in grass that includes applying the above control agent to the soil or the foliage of the weed.

Means to Solve the Problems

As a result of investigations aimed at achieving the above object, the inventors of the present invention discovered that a 1,5-diphenyl-1H-1,2,4-triazole-3-carboxamide derivative represented by formula (1) shown below exhibited a high level of safety to grasses, had a powerful herbicide effect, via either a soil treatment or a foliar treatment, on broadleaf perennial weeds that have proven difficult to control with conventional herbicides for grass and/or on weeds having resistance to conventional herbicides, and was a herbicide active ingredient that had a broad timeframe for optimum treatment, and they were therefore able to complete the present invention.

According to a first aspect of the present invention, there is provided a broadleaf perennial weed control agent for grass that includes, as an active ingredient, a 1,5-diphenyl-1H-1,2,4-triazole-3-carboxamide derivative represented by formula (1) shown below:

[Chemical Formula 1]

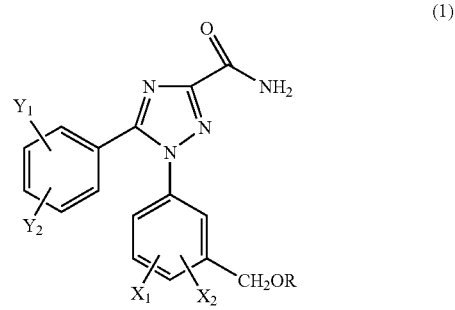

(1)

wherein R represents an alkyl group of 1 to 10 carbon atoms that may be substituted with a fluorine atom, an alkyl group of 1 to 3 carbon atoms that has been substituted with a cycloalkyl group of 3 to 7 carbon atoms, a phenyl group that may have a substituent, or an aralkyl group of 7 to 9 carbon atoms that may have a substituent, $X_1$ represents a halogen atom or an alkyl group of 1 to 3 carbon atoms, $X_2$ represents a hydrogen atom or a halogen atom, and $Y_1$ and $Y_2$ each independently represents a hydrogen atom or a fluorine atom.

In the control agent of the present invention, the grass is preferably at least one type of grass selected from the group consisting of *Zoysia japonica, Zoysia tenuifolia, Zoysia matrella*, Bermuuda grass, Saint Augustine grass, creeping bentgrass, Kentucky bluegrass, perennial ryegrass and fescue, and the broadleaf perennial weed is preferably at least one type of weed selected from the group consisting of *Equisetum arvense, Lespedeza juncea, Trifolium repens, Oxalis comiculata, Viola verecunda, Hydrocotyle, Plantago asiatica, Erigeron philadelphicus, Ixeris stolonifera, Taraxacum* and *Artemisia*.

According to a second aspect of the present invention, there is provided a method for controlling broadleaf perennial weeds in grass, the method including applying the broadleaf perennial weed control agent for grass of the present invention either to the soil or to the foliage of the weed.

Effect of the Invention

The broadleaf perennial weed control agent for grass according to the present invention exhibits a powerful herbicide effect on broadleaf perennial weeds that have proven difficult to control with conventional herbicides for grass and on weeds having resistance to conventional herbicides, and the control effect manifests rapidly. Furtheuuore, the control agent also exhibits a high level of safety to grasses.

The control method of the present invention enables a powerful herbicide effect to be obtained for broadleaf perennial weeds that have proven difficult to control with conventional herbicides for grass and for weeds having resistance to conventional herbicides, while being safe for grasses.

Best Mode for Carrying out the Invention

A more detailed description of the present invention is presented below.

1) Broadleaf Perennial Weed Control Agent for Grass

The broadleaf perennial weed control agent for grass according to the present invention (hereafter also referred to as "the control agent of the present invention") contains a 1,5-diphenyl-1H-1,2,4-triazole-3-carboxamide derivative represented by formula (1) as an active ingredient.

In formula (1), R represents an alkyl group of 1 to 10 carbon atoms that may be substituted with a fluorine atom, an alkyl group of 1 to 3 carbon atoms that has been substituted with a cycloalkyl group of 3 to 7 carbon atoms, an aralkyl group of 7 to 9 carbon atoms that may have a substituent, or a phenyl group that may have a substituent.

Examples of the alkyl group of 1 to 10 carbon atoms that may be substituted with a fluorine atom represented by R include alkyl groups of 1 to 10 carbon atoms such as a methyl group, ethyl group, n-propyl group, isopropyl group, n-butyl group, isobutyl group, sec-butyl group, t-butyl group, n-pentyl group, n-hexyl group, n-heptyl group, n-octyl group, n-nonyl group and n-decyl group; and alkyl groups of 1 to 10 carbon atoms that have been substituted with one or more fluorine atoms, such as a fluoromethyl group, difluoromethyl group, trifluoromethyl group, 2,2,2 trifluoromethyl group 2,2, 2-trifluoroethyl group, pentafluoroethyl group, perfluoropropyl group, perfluorobutyl group and perfluoropentyl group.

Examples of the alkyl group of 1 to 3 carbon atoms within the alkyl group of 1 to 3 carbon atoms that has been substituted with a cycloalkyl group of 3 to 7 carbon atoms include a methyl group, ethyl group, n-propyl group and isopropyl group.

Examples of the cycloalkyl group of 3 to 7 carbon atoms include a cyclopropyl group, cyclopentyl group and cyclohexyl group.

Specific examples of the alkyl group of 1 to 3 carbon atoms that has been substituted with a cycloalkyl group of 3 to 7 carbon atoms include a cyclopropylmethyl group, cyclopentylmethyl group, cyclohexylmethyl group, 2-cyclopropylethyl group, 2-cyclopentylethyl group, 2-cyclohexylethyl group, 3-cyclopropylpropyl group, 3-cyclopentylpropyl group and 3-cyclohexylpropyl group.

Examples of the aralkyl group of 7 to 9 carbon atoms within the aralkyl group of 7 to 9 carbon atoms that may have a substituent include a benzyl group, phenethyl group and 3-phenylpropyl group.

Examples of the substituent within the aralkyl group of 7 to 9 carbon atoms that may have a substituent and the phenyl group that may have a substituent include a halogen atom such as a fluorine atom, chlorine atom or bromine atom, an alkyl group of 1 to 6 carbon atoms such as a methyl group or ethyl group, an alkoxy group of 1 to 6 carbon atoms such as a methoxy group or ethoxy group, a nitro group, and a cyano group.

Further, the aralkyl group and the phenyl group may be substituted with a plurality of substituents, which may be either the same or different.

$X_1$ represents a halogen atom or an alkyl group of 1 to 3 carbon atoms. Examples of the halogen atom for $X_1$ include a fluorine atom, chlorine atom and bromine atom. Furthermore, examples of the alkyl group of 1 to 3 carbon atoms include a methyl group, ethyl group, n-propyl group and isopropyl group.

$X_2$ represents a hydrogen atom or a halogen atom.

Examples of the halogen atom for $X_2$ include a fluorine atom, chlorine atom and bromine atom.

$Y_1$ and $Y_2$ each independently represents a hydrogen atom or a fluorine atom.

Specific examples of the 1,5-diphenyl-1H-1,2,4-triazole-3-carboxamide derivative represented by formula (1) include the compounds disclosed in Japanese Unexamined Patent Application, First Publication No. S63-313779 (Table 1 within the specification).

Of these, flupoxam is particularly preferred as the 1,5-diphenyl-1H-1,2,4-triazole-3-carboxamide derivative represented by formula (1).

The control agent of the present invention exhibits a high level of safety to grasses, has a powerful herbicide effect, via either a soil treatment or a foliar treatment, on broadleaf perennial weeds that have proven difficult to control with conventional herbicides for grass and/or on weeds having resistance to conventional herbicides, and is a control agent that has a broad timeframe for optimum treatment.

There are no particular restrictions on the grass on which the control agent of the present invention may be used, provided the grass is a turf grass. Examples include warm-season grasses selected from the group consisting of *Zoysia japonica, Zoysia tenuifolia, Zoysia matrella*, Bermuda grass, and Saint Augustine grass; and cold-season grasses selected from the group consisting of creeping bentgrass, Kentucky bluegrass, perennial ryegrass and fescue.

Of these, *Zoysia tenuifolia* and *Zoysia japonica* are preferred. *Zoysia tenuifolia* is particularly ideal.

Examples of the weeds that represent the target for the control agent of the present invention include gramineous annual weeds and broadleaf weeds. The broadleaf perennial weed control agent for grass according to the present invention is particularly suitable for targeting broadleaf weeds, and more preferably for targeting broadleaf perennial weeds. Of such broadleaf perennial weeds, one or more weeds selected from the group consisting of *Equisetum arvense, Lespedeza juncea, Trifolium repens, Oxalis corniculata, Viola verecunda, Hydrocotyle, Plantago asiatica, Erigeron philadelphicus, Ixeris stolonifera, Taraxacum* and *Artemisia* is preferably the control target. Of these weeds, the control agent is particularly applicable to *Oxalis corniculata, Viola verecunda*, and *Plantago asiatica*.

The control agent of the present invention also exhibits an excellent control effect on weeds having so-called herbicide resistance.

Examples of weeds in Japan that exhibit resistance to conventional herbicides are disclosed in detail, for example, on the home page of the JHRWG (Japan Herbicide Resistance Working Group). Further, all manner of weeds having herbicide resistance are also disclosed on the home page and the like of the Herbicide Resistance Action Committee, and these weeds represent a large problem in terms of weed control.

Specific examples of these types of weeds having herbicide resistance include weeds that have resistance to the quaternary ammonium-based herbicide "paraquat", for which the main mechanism is known to involve the generation of active oxygen radicals by light, weeds that have resistance to the triazine-based herbicide "simazine", for which the main mechanism is known to involve photosynthesis inhibition, weeds that have resistance to sulfonylurea-based herbicides, for which the main mechanism is known to involve inhibition of branched amino acid biosynthesis (ALS), and weeds that have resistance to the dinitroaniline-based herbicide "trifluralin", which is a known microtubule polymerization inhibitor.

Examples of known weeds that have resistance to the aforementioned quaternary ammonium-based herbicide "paraquat" include *Erigeron philadelphicus, Erigeron canadensis, Conyza sumatrensis, Youngia japonica, Conyza bonariensis* and *Gnaphalium pensylvanicum* of the genus *Conyza*. These weeds are known to exhibit resistance via a development of an active oxygen removal system (SOD), and are also known to exhibit similar resistance to nitrodiphenyl ether-based and cyclic imide-based Protox inhibitors, which have a similar mechanism.

Examples of known weeds that have resistance to the aforementioned triazine-based herbicide "simazine" include Poa arum and the like.

Examples of known weeds that have resistance to the aforementioned sulfonylurea-based herbicides include *Monochoria korsakowii, Lindernia dubia* var. *dubia, Lindernia dubia, Lindernia micrantha, Lindernia procumbens, Elatine triandra, Limnophila sessiliflora, Rotala indica, Scirpus juncoides, Monochoria vaginalis, Scirpus wallichii, Sagittaria trifolia* and *Alopecurus aequalis*.

Examples of known weeds that have resistance to the aforementioned dinitroaniline-based herbicide "trifluralin" include *Alopecurus aequalis* and the like.

Of the above herbicide-resistant weeds, examples of weeds that can be particularly favorably targeted by the control agent of the present invention include weeds of the genus *Conyza* and *Poa annua*, the seeds of which are spread by the wind and propagate readily within grasses. Other examples include weeds that have resistance to sulfonylurea-based herbicides.

It is predicted that, in future years, many weeds having herbicide resistance will appear in Japan. However, it is expected that the control agent of the present invention will exhibit a powerful effect on these weeds that develop resistance to herbicide treatments other than the control agent of the present invention.

Herbicide resistance generally develops when herbicides having the same machanism are used repeatedly. Although the mechanism of the 1,5-diphenyl-1H-1,2,4-triazole-3-carboxamide derivative represented by formula (1) that is included within the control agent of the present invention as an active ingredient is not entirely clear, the compound exhibits a satisfactory control effect on weeds having resistance to conventional herbicides by a single soil or foliar treatment.

From the viewpoints of achieving an even more powerful control effect and preventing the appearance of new resistance, a mixed treatment, systemic treatment or repeated treatment using a combination of the control agent of the present invention and another agrichemical active ingredient is preferred. Moreover, combining the control agent of the present invention with an integrated pest management (IPM) system that includes cultural weed control such as mowing is also preferred. Employing these types of treatments also means the applied dose of the control agent of the present invention can be reduced.

There are no particular restrictions on the agrichemical active ingredients that may be mixed with the control agent of the present invention, and these other active ingredients may be liquid or solid, organic compounds or inorganic compounds, and may be either a single compound or a mixture of compounds. Specific examples of these other active ingredients include the fungicides, insecticides, acaricides, plant growth regulators and herbicides listed below. Any of these agrichemical active ingredients may be used individually, or a mixture of two or more different ingredients may be used. By using a mixture, additive effects and dramatic synergistic effects can be obtained on the development of weeds having potency, toxicity and resistance.

Fungicides:

Copper agents: basic copper chloride, basic copper sulfate and the like;

Sulfur agents: thiuram, zineb, maneb, mancozeb, ziram, propineb, polycarbamate and the like;

Polyhaloalkylthio agents: captan, folpet, dichlorfluanido and the like;

Organochlorine agents: chlorothalonil, phthalide and the like;

Organophosphorous agents: IBP, EDDP, trichlofos methyl, pyrazophos, fosetyl and the like;

Benzimidazole agents: thiophanate-methyl, benomyl, carbendazim, tiabendazole and the like;

Dicarboximide agents: iprodione, procymidone, vinclozolin, fluoroimide and the like;

Carboxamide agents: oxycarboxin, mepronil, flutolanil, tecloftalam, trichlamide, pencycuron, thifluzamide, penthiopyrad and the like;

Acylalanine agents: metalaxyl, oxadixyl, furalaxyl and the like;

Methoxy acrylate agents: kresoxim-methyl, azoxystrobin, metominostrobin and the like;

Anilinopyrimidine agents: andoprin, mepanipyrim, pyrimethanil, diprozinil and the like;

SBI agents: triadimefon, triadimenol, bitertanol, myclobutanil, hexaconazole, propiconazole, triflurnizole, prochloraz, pefurazoate, fenarimol, pyrifenox, triforine, flusilazole, etaconazole, dichlobutorazol, fluotrimazole, flutriafen, penconazole, diniconazole, imazalil, tridemorph, fenpropimorph, buthiobate, epoxiconazole, metoconazole and the like;

Antibiotic agents: polyoxins, blastieidin-S, kasugamycin, validamycin, dihydrostreptomycin sulfate and the like; and Other fungicides: propamocarb hydrochloride, quintozene, hydroxyisoxazole, anilazine, isoprothiolane, probenazole, chinomethionat, dithianon, dinocap, diclomezine, ferimzone, fluazinam, pyroquilon, tricyclazole, oxolinic acid, dithianon, iminoctadine acetate, cymoxanil, pyrrolnitrin, methasulfocarb, diethofencarb, binapacryl, lecithin, sodium bicarbonate, fenaminosulf, dodine, dimethomorph, phenazine oxide, carpropamid, flusulfamide, fludioxonil, famoxadon and the like.

Insecticides/Acaricides:

Organophosphorous and carbamate-based insecticides: fenthion, fenitrothion, diazinon, chlorpyrifos, ESP, vamidothion, phenthoate, dimethoate, formothion, malathion, trichlorfon, thiometon, phosmet, dichlorvos, acephate, EPBP, methyl parathion, oxydemeton-methyl, ethion, salithion, cyanophos, isoxathion, pyridafenthion, phosalone, methidathion, sulprofos, chlorfenvinphos, tetrachlorvinphos, dimethylvinphos, propaphos, isofenphos, ethylthiometon, profenofos, pyraclofos, monocrotophos, azinphos-methyl, aldicarb, methomyl, thiodicarb, carbofuran, carbosulfan, benfuracarb, furathiocarb, propoxur, BPMC, MTMC, MIPC, carbaryl, pirimicarb, ethiofencarb, fenoxycarb and the like;

Pyrethroid-based insecticides: permethrin, cypermethrin, deltamethrin, fenvalerate, fenpropathrin, pyrethrins, allethrin, tetramethrin, resmethrin, dimethrin, propathrin, phenothrin, prothrin, fluvalinate, cyfluthrin, cyhalothrin, flucythrinate, etofenprox, cycloprothrin, tralomethrin, silafluofen, brofenprox, acrinathrin and the like;

Neonicotinoid-based compounds;

Benzoylurea-based and other insecticides: diflubenzuron, chlorfluazuron, hexaflumuron, triflumuron, flufenoxuron, flucycloxuron, buprofezin, pyriproxyfen, methoprene, benzoepin, diafenthiuron, acetamiprid, imidacloprid, nitenpyram, fipronil, cartap, thiocyclam, bensultap, nicotine sulfate, rotenone, metaldehyde, machine oil, BT, insect pathogen viruses and other microbial agrichemicals, and pheromone agents and the like.

Nematicides: fenamiphos, fosthiazate and the like.

Acaricides: chlorobenzilate, phenisobromolate, dicofol, amitraz, BPPS, benzomate, hexathiazox, fenbutatin oxide, polynactin, quinomethionate, CPCBS, tetradifon, abamectin, milbemectin, clofentezine, cyhexatin, pyridaben, fenpyroximate, tebufenpyrad, pyrimidifen, fenothiocarb, dienochlor and the like, Plant growth regulators: gibberellins (such as gibberellin A3, gibberellin A4 and gibberellin A7), IAA, NAA and the like.

Herbicides: acifluorofen, atrazine, alachlor, isoxaben, isoproturon, imazaquin, imazethapyr, imazosulfuron, ethoxysulfuron, ethofumesate, endothal, oxadiazon, oxadiargyl, oryzalin, orthobencarb, cafenstrole, quinoclamine, quinclorac, glyphosate, glyphosinate, clomazone, chlorprofam, zaitoron, cyanazine, diuron, dicamba, cyclosulfamuron, dichlobenil, diclofop-methyl, cinosulfuron, diflufenican, dithiopyr, difenzoquat, cinmethylin, sulcotrione, sethoxydim, difenzoquat, daimuron, thiobencarb, thenylchlor, tralkoxydim, triaziflam, triazofenamide, triclopyr, trifluralin, tolyfloxysulfuron, naproanilide, napropamide, nicosulfuron, banafin, paraquat, halosulfuron-methyl, bifenox, piperophos, pyrazolate, pyrithiobac, pyridate, pyributicarb, fenoxaprop-ethyl, fenmedifam, butamiphos, flazasulfuron, flamprop-ethyl, flumiclorac-pentyl, fluthiacet-methyl, flumetsulam, pretilachlor, prodiamine, propanil, propyzamide, florasuram, bromoxynil, bethrodine, pendimethalin, bensulfuron-methyl, benzoylprop-ethyl, bentazone, pendimethalin, benfuresate, fomesafen, metamitron, metsulfuron-methyl, metribuzin, rimsulfuron, lenacil, ACN, CAT, DCBN, EPTC, MCPP, MDBA, 2,4-D, and 2,4-DB and the like.

Synergists/Antidotes/Detoxifying agents: octachlorodipropyl ether, piperonyl butoxide, cyneprin, IBTA, benoxacor, cloquintocet, ciometranil, dichlormid, fenchlorazole-ethyl, fencloram, flurazole, flaxofenimi, furilazole, mefenpyr-diethyl, MG191, naphthalic anhydride, and oxabetrinil and the like.

Antibacterial/Antifungal/Antialgal agents: trialkyltriamine, ethanol, isopropyl alcohol, propyl alcohol, trisnitro, chlorobutanol, pronopol, glutaraldehyde, fouualdehyde, α-bromocinnamaldehyde, scare M-8, caisson CG, NS-500W, BIT, n-butyl BIT, allyl isothiocyanate, thiobendazole, methyl 2-benzimidazolyl carbamate, lauricidine, biovan, triclocarban, halocarban, glasis car, benzoic acid, sorbic acid, caprylic acid, propionic acid, 10-undecylenic acid, potassium sorbate, potassium propionate, potassium benzoate, monomagnesium phthalate, zinc undecylenate, 8-hydroxyquinoline, copper quinoline, TMTD, triclosan, diclohelanilide, tolyfluanid, milt protein, egg white lysozyme, benthiazole, sodium carbam, triazine, tebuconazole, hinokithiol, tetrachloroisophthalonitrile, tectamer 38, chlorhexidine gluconate, chlorhexidine hydrochloride, polyhexamethylene biguanide, polybiguanide hydrochloride, danthoprom, clidant, sodium pyrithion, zinc pyrithion, densil, kappa-pyrithion, thymol, isopropyl methyl phenol, OPP, phenol, butyl paraben, ethyl paraben, methyl paraben, propyl paraben, meta-cresol, ortho-cresol, para-cresol, sodium ortho-phenylphenol, chlorofen, parachlorophenol, parachloromethaxylate, parachlorocresol, fluorfolpet, polylysine, biopan P-1487, Jote methyl paratolylsulfone, polyvinylpyrrolidone parachloroisocyanel, hydrogen peroxide, stabilized chlorine dioxide, peracetic acid, copper naphthenate, Novalon AG 300, silver chloride, titanium oxide, silver, zinc-calcium phosphate, Silver Ace, silver-zinc aluminosilicate, silver-zinc zeolite, Novalon AGZ330, phorone killer, dimer 136, benzalkonium chloride, didecyldimethylammonium chloride, Bardac 2250/80, benzotonium chloride, Hyamine 3500J, cetylammonium bromide, cetrimide, CTAB, Cetavlon, Dimer-38, benzalkonium chloride, Bardac 170P, DC-5700, cetylpyridinium chloride, chitosan, deuron, DCMU, Prepentol A6, CMI, 2Cl-OIT, BCM, ZPT, BNP, OIT, IPBC, and TCMSP and the like.

Of these, in the present invention, the aforementioned agrichemical active ingredient is preferably a herbicide for grass such as ACN, CAT, DCBN, MCPP, MDBA, alachlor, isoxaben, imazaquin, imazosulfuron, ethoxysulfuron, endothal, oxadiargyl, oryzalin, orthobencarb, cafenstrole, quinoclamine, zaitoron, cyclosulfamuron, dithiopyr, cinosulfuron, cinmethylin, thenylchlor, triaziflam, triclopyr, tolyfloxysulfuron, napropamide, banafin, halosulfuron-methyl, bifenox, pyributicarb, butamiphos, flazasulfuron, prodiamine, propyzamide, florasuram, bethrodine, pendimethalin, metsulfuron-methyl, rimsulfuron and lenacil.

Furthermore, ingredients other than agrichemicals, including other agricultural materials such as fertilizers, plant activators and colorants and the like may be included in mixed formulations, joint treatments or systemic treatments or the like.

The control agent of the present invention is typically mixed with an organic solvent, an extender, and water and the like, a surfactant or other formulation assistant is added if required, and a formulation is prepared in the form of a wettable powder, water-dispersible granules, dust, aerosol, suspension, emulsion, suspoemulsion, microcapsules, microemulsion or paste-like formulation.

As the surfactant, any of the surfactants typically used in agrichemical formulations can be used without any particular restrictions. This includes nonionic surfactants, anionic surfactants, cationic surfactants and amphoteric surfactants.

Examples of nonionic surfactants include sugar ester-type surfactants such as sorbitan fatty acid esters (C12 to C18), POE sorbitan fatty acid esters (C12 to C18) and sucrose fatty acid esters; fatty acid ester-type surfactants such as POE fatty acid esters (C12 to C18), POE resin acid esters and POE fatty acid diesters (C12 to C18); alcohol-type surfactants such as POE alkyl ethers (C12 to C18); alkylphenol-type surfactants such as POE alkyl (C8 to C12) phenyl ethers, POE dialkyl (C8 to C12) phenyl ethers and POE alkyl (C8 to C12) phenyl ether formalin condensation products; polyoxyethylene-polyoxypropylene block polymer-type surfactants such as polyoxyethylene-polyoxypropylene block polymers and alkyl (C12 to C18) polyoxyethylene-polyoxypropylene block polymer ethers; alkyl amine-type surfactants such as POE alkyl amines (C12 to C18) and POE fatty acid amides (C12 to C18); bisphenol-type surfactants such as POE fatty acid bisphenyl ethers; polyaromatic cyclic surfactants such as POA benzyl phenyl (or phenylphenyl) ether and POA styryl phenyl (or phenylphenyl) ether; silicon-based and fluorine-based surfactants such as POE ether and ester-type silicon and fluorine-based surfactants; and vegetable oil-based surfactants such as POE castor oil and POE hardened castor oil.

Examples of anionic surfactants include sulfate-type surfactants such as alkyl sulfates (C12 to C18, Na, $NH_4$, alkanolamine), POE alkyl ether sulfates (C12 to C18, Na, $NH_4$, alkanolamine), POE alkyl phenyl ether sulfates (C12 to C18, $NH_4$, alkanolamine, Ca), POE benzyl (or styryl)phenyl (or phenylphenyl)ether sulfates (Na, $NH_4$, alkanolamine), and polyoxyethylene-polyoxypropylene block polymer sulfates (Na, $NH_4$, alkanolamine); sulfonate-type surfactants such as paraffin (alkane) sulfonates (C12 to C22, Na, Ca, alkanolamine), AOS (C14 to C16, Na, alkanolamine), dialkyl sulfosuccinates (C8 to C12, Na, Ca, Mg), alkylbenzene sulfonates (C12, Na, Ca, Mg, $NH_4$, alkylamine, alkanolamine, cyclohexylamine), mono- or dialkyl (C3 to C6) naphthalene sulfonates (Na, $NH_4$, alkanolamine, Ca, Mg), naphthalene sulfonate-formalin condensation products (Na, $NH_4$), alkyl (C8 to C12) diphenyl ether disulfonates (Na, $NH_4$), lignin sulfonates (Na, Ca), POE alkyl (C8 to C12) phenyl ether sulfonates (Na) and POE alkyl (C12 to C18) ether sulfosuccinic acid half esters (Na); POE alkyl (C12 to C18) ether phosphates (Na, alkanolamine) such as carboxylic acid-type fatty acid salts (C12 to C18, Na, K, $NH_4$, alkanolamine), N-methyl-fatty acid sarcosinates (C12 to C18, Na), resin acid salts (Na, K); and phosphate-type surfactants such as POE mono- or dialkyl (C8 to C12) phenyl ether phosphates (Na, alkanolamine), POE benzylated (or styrylated) phenyl (or phenylphenyl)ether phosphates (Na, alkanolamine), polyoxyethylene-polyoxypropylene block polymers (Na, alkanolamine), phosphatidyl choline-phosphatidyl ethanolimines (lecithin) and alkyl (C8 to C12) phosphates.

Examples of cationic surfactants include ammonium-type surfactants such as alkyltrimethylammonium chlorides (C12 to C18), methyl-polyoxyethylene-alkylammonium chlorides (C12 to C18), alkyl-N-methylpyridium bromides (C12 to C18), mono- or dialkyl (C12 to C18) methylated ammonium chlorides, and alkyl (C12 to C18) pentamethyl propylene diamine dichlorides; and benzalkonium-type surfactants such as alkyldimethylbenzalkonium chlorides (C12 to C18) and benzethonium chlorides (octylphenoxyethoxyethyldimethylbenzylammonium chlorides).

Examples of amphoteric surfactants include betaine-type surfactants such as dialkyl (C8 to C12) diaminoethyl betaines and alkyl (C12 to C18) dimethylbenzyl betaines; and glycine-type surfactants such as dialkyl (C8 to C12) diaminoethyl glycines and alkyl (C12 to C18) dimethylbenzyl glycines.

Any one these surfactants may be used alone, or two or more different surfactants may be used in combination.

Examples of the organic solvent used in an emulsion, suspoemulsion, microcapsule formulation or microemulsion formulation include vegetable oils; petroleum-based linear hydrocarbons; aromatic hydrocarbons such as alkylated naphthalenes, and preferably α-methylnaphthalene; aliphatic or alicyclic hydrocarbons such as paraffin or cyclohexane; glycols and ethers thereof such as propylene glycol, dipropylene glycol, ethylene glycol, ethylene glycol monomethyl ether or monoethyl ether; esters such as methyl oleate and dibasic acid (adipic acid, glutaric acid, succinic acid) dimethyl esters; ketones such as cyclohexanone, isophorone or diacetone alcohol; and heterocyclic compounds such as N-methyl-2-pyrrolidone and y-butyrolactone. These solvents may be used individually, or as a mixture containing two or more different solvents.

Examples of the extender (carrier) used in a wettable powder, water-dispersible granules or dust include inorganic salts such as potassium chloride, phosphate salts, hydrogen phosphate salts, and ammonium sulfate; natural mineral powders; and inorganic synthetic extenders having superior oil absorption such as silicon oxides. Furthermore, sugars such as sucrose and lactose; and other organic materials such as urea, starch, dextrin, cellulose, cellulose derivatives, grain powders and sawdust may also be used as the extender. These extenders may be used individually, or as a mixture containing two or more different extenders.

An antifreeze agent may also be added to the control agent of the present invention. Specific examples of antifreeze agents include ethylene glycol, propylene glycol, glycerin diethylene glycol and dipropylene glycol, and these may be used either individually or in mixtures containing two or more different antifreeze agents.

Furthermore, in an emulsion or a suspension concentrate, a thickener such as a hydroxyalkyl cellulose or cellulose derivative thereof such as a metal salt, a polyvinyl alcohol derivative, polyvinylpyrrolidone, natural gum or bentonite may also be added to the control agent to prevent precipitation and separation of the agrichemical active ingredient(s).

Inorganic salts such as calcium carbonate, potassium chloride and sodium sulfate; organic acids such as citric acid, malic acid, fumaric acid and stearic acid, and salts thereof; sugars such as lactose and sucrose; inorganic additives such as alumina powder, silica gel, zeolite, hydroxyapatite, zirconium phosphate, titanium phosphate, titanium oxide, zinc oxide, hydrotalcite, kaolinite, montmorillonite, talc and clay; antioxidants such as n-propyl gallate and butylhydroxyanisole; pH regulators and buffering agents such as sodium tripolyphosphate, sodium dihydrogenphosphate and ammonium phosphate; colorants such as blue food coloring No. 1, methylene blue and pigment red 48; preservatives; lubricants; ultraviolet absorbers; antistatic agents and the like may also be added to the control agent of the present invention as required.

The control agent of the present invention may also include solid or liquid auxiliary agents such as stabilizers, including solid paraffin, liquid paraffin, epoxidized or non-epoxidized vegetable oils (such as epoxidized coconut oil, rapeseed oil, or soybean oil), antifoaming agents (such as silicone oil), viscosity regulators, binders, adhesives, and other active ingredients (such as microbicidal agents, anti-mold agents, bacetricidal agents, insecticides and acaricides).

The control agent of the present invention can be produced using conventional methods.

For example, in those cases where the control agent of the present invention is an emulsion (oil in water), either a solution containing the active ingredient(s), an emulsifier and an emulsion stabilizer dissolved in an organic solvent is added to water while a homogenization is performed, or water is added gradually to a solution containing the active ingredient(s), an emulsifier and an emulsion stabilizer dissolved in an organic solvent while a homogenization is performed.

In the case of a suspension concentrate, the control agent can be produced by mixing the active ingredient(s) with a wetting agent, dispersant, thickener, preservative, and antifoaming agent and the like, and then crushing the resulting mixture in a wet grinding mill filled with beads.

In the case of a suspoemulsion, the control agent can be produced by using a three-one motor or the like to mix together an emulsion (oil in water) and a suspension concentrate.

In the case of a wettable powder, the control agent can be produced by air grinding using a jet mill such as an Ulmax (manufactured by Nisso Engineering Co., Ltd.).

Furthermore, in the case of water-dispersible granules, the control agent can be produced by adding water to a wettable powder, and then performing kneading, extruding and drying to form the granules. A dust can be produced by mixing the active ingredient(s) with a portion of an extender and any other components, crushing the mixture in a jet mill to prepare a concentrated powder, and then diluting this concentrated powder by mixing with the remainder of the extender.

The prepared formulation of the control agent of the present invention can be applied to seeds, plants, water surfaces or soil, either as is, or in a diluted form with water. Furthermore, the control agent formulation may also be used in combination with other fungicides, herbicides, fertilizers, or soil improvers or the like. The dosage used for the agricultural composition of the present invention varies depending on factors such as the mixing ratio of the two active ingredients, atmospheric conditions, formulation type, application method, application locus, target disease for the control and target crop, but is typically regulated so that the amount of the active ingredient compound applied per hectare is within a range from 1 to 1,000 g, and preferably from 10 to 100 g.

The application methods and application seasons for the control agent of the present invention can be conducted using typical application machinery and application methods used with conventional agrichemicals.

Highly effective control of broadleaf perennial weeds can be achieved by application of the control agent either prior to weed germination or following weed germination, although in order to achieve a particularly superior effect, a foliar treatment conducted once most of the seeds have germinated enables good absorption of the control agent and long-term suppression of new growth, and is therefore particularly desirable. Similar effects can also be achieved for weeds other than broadleaf perennial weeds by

EXAMPLES

A more detailed description of the present invention is presented below based on a series of examples, although the scope of the present invention is in no way limited by the following examples.

Example 1

Production of 50.6% by Weight Flupoxam Water-Dispersible Granules 50.6 parts by weight of flupoxam (1-[4-chloro-3-[(2,2,3,3,3-pentafluoropropoxy)methyl]phenyl]-5-phenyl-1H-1,2,4-triazole-3-carboxamide), 1.0 part by weight of sodium lauryl sulfate (product name: Newkalgen LX-C, manufactured by Takemoto Oil & Fat Co., Ltd.), 10.0 parts by weight of potassium chloride, 27A parts by weight of diatomaceous earth (product name: Kunilite 201, manufactured by Kunimine Industries Co., Ltd.), 6.0 parts by weight of the sodium salt of a naphthalenesulfonic acid formaldehyde condensation product (product name: Newkalgen PS-P, manufactured by Takemoto Oil & Fat Co., Ltd.), and 5.0 parts by weight of a metal polycarboxylate (product name: Newkalgen WG-5, manufactured by Takemoto Oil & Fat Co., Ltd.) were mixed together, the resulting mixture was crushed in a hammer mill, 45 parts of water was added to the crushed mixture, and the mixture was kneaded, extruded using a 0.7 mm screen, and then granulated and dried at 70° C. for 24 hours. The portion of these granules remaining on sieves of 0.59 to 0.84 mm was then collected, yielding flupoxam 50.6% by weight water-dispersible granules. The thus obtained water-dispersible granules were termed "formulation A".

For the purposes of comparison, the following commercially available formulations were used.

Formulation B: prodiamine 63% water-dispersible granules (product name: Kusablock, manufactured by Syngenta AG)

Formulation C: dithiopyr 32% emulsion (product name: Dictran, manufactured by Dow AgroSciences LLC)

Formulation D: MCPP 50% liquid formulation (product name: MCPP, manufactured by Maruwa Biochemical Co., Ltd.)

Formulation E: 2,4-D amine salt 49.5% liquid formulation (product name: 2,4-D [Ishihara] amine salt, manufactured by Ishihara Sangyo Kaisha, Ltd.)

Formulation F: bifenox 38% flowable formulation (product name: Wirral, manufactured by Bayer CropScience Ltd.)

Formulation G: pendimethalin 45% flowable formulation (product name: Wayup, manufactured by BASF Corporation)

Test examples relating to the effects of the control agent of the present invention are presented below.

The control effect was evaluated in accordance with the criteria listed below, and recorded as a weed kill index.

| Evaluation criteria | |
| --- | --- |
| Weed kill rate | Weed kill index |
| 0% | 0 |
| 20 to 29% | 2 |
| 40 to 49% | 4 |
| 60 to 69% | 6 |
| 80 to 89% | 8 |
| 100% | 10 |

Furthermore, indices of 1, 3, 5, 7 and 9 represent the middle values between 0 and 2, 2 and 4, 4 and 6, 6 and 8, and 8 and 10 respectively.

[Numerical Equation 1]

$$\text{Weed kill rate (\%)} = \frac{\text{(Live ground species in untreated area} - \text{Live ground species in treated area)}}{\text{Live ground species in untreated area}} \times 100$$

(Control Agent Test 1) Control Effect on *Viola verecunda* (a Broadleaf Perennial Weed)

A 2 m² partitioned area was created within an area of *Viola verecunda* growth at a golf course in Ichihara city in Chiba prefecture. The water-dispersible granules produced in example 1 were diluted with tap water to prepare a spray liquid.

This spray liquid was sprayed onto the foliage at an application water rate of 300 ml/m² using a small sprayer. The sprayed area was then inspected at two-weekly intervals, and the degree of the control activity was noted. The test results are shown in Table 1. The results of the test demonstrated that *Viola verecunda*, which was impossible to control with the other formulations, was able to be controlled with the formulation A (flupoxam 50.6% by weight water-dispersible granules).

TABLE 1

| Formulation | Dosage (g/m$^2$) | Control effect (Number of weeks elapsed from application) | | | | |
|---|---|---|---|---|---|---|
| | | 2 | 4 | 6 | 8 | 10 |
| A | 0.2 | 4 | 10 | 10 | 10 | 10 |
| | 0.3 | 6 | 10 | 10 | 10 | 10 |
| B | 0.125 | 0 | 0 | 0 | 0 | 0 |
| C | 0.15 | 0 | 0 | 0 | 0 | 0 |
| D | 1 | 4 | 0 | 0 | 0 | 0 |
| E | 0.5 | 2 | 0 | 0 | 0 | 0 |
| F | 1 | 6 | 2 | 0 | 0 | 0 |
| Untreated | — | 0 | 0 | 0 | 0 | 0 |

(Control Agent Test 2) Test to Confirm Control Effect on *Plantago asiatica*

The water-dispersible granules produced in example 1 were diluted with tap water to prepare a spray liquid. A pot was prepared in advance by sowing *Plantago asiatica* seeds in the soil, and then covering the seeds with soil. The soil was then sprayed with the spray liquid using an application water rate of 200 ml/m$^2$. The sprayed pot was then placed inside a glass house and inspected approximately once a week, and the degree of the control activity was noted. The test results are shown in Table 2. From Table 2 it is clear that when the control agent of example 1 (formulation A) was applied, perfect control had been achieved within 14 days of the application. In contrast, the other control agents used in the comparative examples (which are all major soil treatment agents) required considerably longer to achieve perfect control.

TABLE 2

| Formulation | Dosage (g/m$^2$) | Control effect (Number of days elapsed from application) | | | | |
|---|---|---|---|---|---|---|
| | | 14 | 21 | 28 | 33 | 50 |
| A | 0.15 | 10 | 10 | 10 | 10 | 10 |
| | 0.2 | 10 | 10 | 10 | 10 | 10 |
| | 0.3 | 10 | 10 | 10 | 10 | 10 |
| B | 0.12 | 7 | 7 | 9 | 9 | 10 |
| | 0.24 | 7 | 6 | 9 | 9 | 10 |
| C | 0.15 | 5 | 7 | 9 | 10 | 10 |
| | 0.3 | 8 | 7 | 9 | 10 | 10 |
| F | 0.4 | 8 | 8 | 9 | 10 | 10 |
| | 0.5 | 9 | 9 | 9 | 10 | 10 |
| | 0.9 | 9 | 8 | 9 | 10 | 10 |

(Control Agent Test 3) Test to Confirm Control Effect on *Plantago asiatica*

Using the spray liquid prepared in the control agent test 2, a control test was conducted on *Plantago asiatica* having a foliar age of 1 to 1.5 L, and a plant height of 0.5 to 1.5 cm. In other words, *Plantago asiatica* seeds were sown in advance and cultivated inside a glass house, and when the prescribed foliar age was reached, the pot was sprayed with the test liquid.

The test results are shown in Table 3. From Table 3 it is evident that when the control agent of example 1 (formulation A) was applied, an almost perfect control effect had been achieved by 28 days after treatment, which represents a faster manifestation of the control effect, and a superior degree of control, than the other control agents (formulations B, C and G) used in the comparative examples.

TABLE 3

| Formulation | Dosage (g/m$^2$) | Control effect (Number of days elapsed from application) | | | | | |
|---|---|---|---|---|---|---|---|
| | | 7 | 14 | 21 | 28 | 33 | 50 |
| A | 0.15 | 7 | 9 | 9 | 10 | 10 | 10 |
| | 0.2 | 7 | 9 | 9 | 10 | 10 | 10 |
| | 0.3 | 6 | 9 | 9 | 10 | 10 | 10 |
| B | 0.12 | 2 | 6 | 7 | 8 | 7 | 8 |
| | 0.24 | 2 | 6 | 7 | 9 | 8 | 9 |
| C | 0.15 | 3 | 7 | 8 | 9 | 9 | 9 |
| | 0.3 | 3 | 7 | 8 | 9 | 9 | 9 |
| G | 0.4 | 3 | 8 | 8 | 9 | 9 | 9 |
| | 0.5 | 3 | 9 | 9 | 9 | 9 | 10 |
| | 0.9 | 3 | 8 | 8 | 9 | 9 | 10 |

(Control Agent Test 4) Test to Confirm Control Effect on *Plantago asiatica*

Using the spray liquid prepared in the control agent test 2, a control test was conducted on *Plantago asiatica* having a foliar age of 2 to 3.5 L, and a plant height of 1.7 to 3.7 cm. In other words, *Plantago asiatica* seeds were sown in advance and cultivated inside a glass house, and when the prescribed foliar age was reached, the pot was sprayed with the test liquid.

The test results are shown in Table 4. From Table 4 it is evident that when the control agent of example 1 (formulation A) was applied, an almost perfect control effect had been achieved by 33 days after treatment. In the case of the other control agents (formulations B, C and G) used in the comparative examples, a perfect control effect was unattainable even after 50 days, confirming that the formulation A offered a superior control effect.

TABLE 4

| Formulation | Dosage (g/m$^2$) | Control effect (Number of days elapsed from application) | | | | | |
|---|---|---|---|---|---|---|---|
| | | 7 | 14 | 21 | 28 | 33 | 50 |
| A | 0.15 | 4 | 8 | 9 | 10 | 10 | 10 |
| | 0.2 | 4 | 8 | 9 | 10 | 10 | 10 |
| | 0.3 | 4 | 8 | 9 | 10 | 10 | 10 |
| B | 0.12 | 1 | 2 | 4 | 6 | 5 | 7 |
| | 0.24 | 1 | 2 | 5 | 6 | 5 | 7 |
| C | 0.15 | 2 | 5 | 6 | 7 | 7 | 9 |
| | 0.3 | 2 | 5 | 6 | 7 | 7 | 9 |
| G | 0.4 | 2 | 5 | 6 | 7 | 7 | 8 |
| | 0.5 | 3 | 5 | 6 | 7 | 8 | 9 |
| | 0.9 | 3 | 5 | 6 | 7 | 7 | 8 |

(Control Agent Test 5) Test to Confirm Control Effect of Foliar Treatment on *Oxalis corniculata*

An outdoor concrete pot (0.5 m×0.5 m, 0.25 m$^2$) was laid with *Zoysia tenuifolia* and cultivated, and *Oxalis corniculata* that seeded naturally within the pot (4 to 5 leafs at the time of treatment) was treated by preparing the prescribed dosages of the test formulations shown in the table below, and then conducting a foliar spray treatment at the application water rate of 200 ml/m$^2$ using a pressurized sprayer.

The treated pots were inspected 18 days after treatment, and then at two-weekly intervals, and the degree of the control activity was noted. The test results are shown in Table 5.

TABLE 5

| Formulation | Dosage (g/m²) | Control effect (Number of days elapsed from application) | | | |
|---|---|---|---|---|---|
| | | 18 | 32 | 46 | 60 |
| A | 0.15 | 1 | 7 | 9 | 10 |
|   | 0.2  | 5 | 8 | 10 | 10 |
|   | 0.3  | 8 | 10 | 10 | 10 |
| B | 0.12 | 0 | 0 | 0 | 0 |
|   | 0.24 | 0 | 0 | 0 | 0 |
| C | 0.15 | 0 | 0 | 0 | 0 |
|   | 0.3  | 0 | 0 | 0 | 0 |
| G | 0.4  | 0 | 0 | 0 | 0 |
|   | 0.9  | 0 | 0 | 0 | 0 |

From Table 5 it is clear that the control agent of example 1 (formulation A) was able to achieve a perfect control effect on *Oxalis corniculata*, within 32 days of treatment when the active ingredient was applied at a dosage of 0.3 g per 1 m², within 46 days of treatment when the active ingredient was applied at a dosage of 0.2 g per 1 m², and within 60 days of treatment when the active ingredient was applied at a dosage of 0.15 g per 1 m².

In contrast, all of the major soil treatment agents (formulations B, C and G) used as comparative formulations exhibited no control effect whatsoever.

Furthermore, although not shown in the table, the control agent of example 1 (formulation A), and the formulations B, C and G all displayed absolutely no detrimental effects on the *Zoysia tenuifolia* during the test period.

From the above results it is clear that the control agent of example 1 (formulation A) differs from the conventional major soil treatment agents for grasses, and is able to effectively control *Oxalis corniculata* by foliar treatment, while exhibiting a high level of safety to *Zoysia tenuifolia*.

The invention claimed is:

1. A method for controlling broadleaf perennial weeds in turf grass, said method comprising: applying a broadleaf perennial weed control agent for turf grass comprising, as an active ingredient, a 1-[4-chloro-3-[(2,2,3,3,3-pentafluoropropoxy)methyl]phenyl-5-phenyl-1H-1,2,4-triazole-3-carboxamide to the soil or the foliage of turf grass containing at least one broadleaf perennial weed.

2. A method for controlling broadleaf perennial weeds in turf grass, said method comprising: applying a broadleaf perennial weed control agent for turf grass, comprising, as an active ingredient, a 1-[4-chloro-3-[(2,2,3,3,3-pentafluoropropoxy)methyl]phenyl-5-phenyl-1H-1,2,4-triazole-3-carboxamide, to the soil or the foliage of turf grass containing at least one broadleaf perennial weed, wherein said turf grass is at least one type of turf grass selected from the group consisting of *Zoysia japonica*, *Zoysia tenuifolia*, *Zoysia matrella*, Bermuda grass, Saint Augustine grass, creeping bentgrass, Kentucky bluegrass, perennial ryegrass and fescue.

3. A method for controlling broadleaf perennial weeds in turf grass, said method comprising: applying a broadleaf perennial weed control agent for turf grass, comprising, as an active ingredient, a 1-[4-chloro-3-[(2,2,3,3,3-pentafluoropropoxy)methyl]phenyl-5-phenyl-1H-1,2,4-triazole-3-carboxamide to the soil or the foliage of turf grass containing at least one broadleaf perennial weed, wherein said broadleaf perennial weed is at least one type of weed selected from the group consisting of *Equisetum arvense*, *Lespedeza juncea*, *Trifolium repens*, *Oxalis corniculata*, *Viola verecunda*, *Hydrocotyle*, *Plantago asiatica*, *Erigeron philadelphicus*, *Ixeris stolonifera*, *Taraxacum* and *Artemisia*.

* * * * *